United States Patent [19]

Sandhaus

[11] Patent Number: 4,877,028

[45] Date of Patent: Oct. 31, 1989

[54] APPARATUS FOR EFFECTING OCCLUSION OF THE VAS DEFERENS

[75] Inventor: Jeffrey Sandhaus, Palisades, N.Y.

[73] Assignee: Vastech Medical Products Inc., New Brunswick, N.J.

[21] Appl. No.: 223,682

[22] Filed: Jul. 25, 1988

Related U.S. Application Data

[63] Continuation of Ser. No. 884,417, Jul. 11, 1986, abandoned.

[51] Int. Cl.[4] .............................................. A61B 17/12
[52] U.S. Cl. .................................... 128/326; 128/305; 128/346
[58] Field of Search ............... 128/303 A, 303 R, 325, 128/326, 346, 340, 334 R, 305

[56] References Cited

U.S. PATENT DOCUMENTS

| | | | |
|---|---|---|---|
| 3,006,344 | 10/1961 | Vogelfanger | 128/346 |
| 3,584,628 | 6/1971 | Green | 128/326 |
| 3,665,924 | 5/1972 | Noiles et al. | 128/326 |
| 3,882,854 | 5/1975 | Hulka et al. | 128/346 |
| 4,394,864 | 7/1983 | Sandhaus | 128/325 |
| 4,428,374 | 1/1984 | Auburn | 128/325 |
| 4,509,517 | 4/1985 | Zibelin | 128/328 |
| 4,569,346 | 2/1986 | Poirier | 128/325 |
| 4,682,598 | 7/1987 | Beraha | 128/326 |

Primary Examiner—C. Fred Rosenbaum
Assistant Examiner—Mark F. Colosimo
Attorney, Agent, or Firm—Lerner, David, Littenberg, Krumholz & Mentlik

[57] ABSTRACT

Apparatus for accomplishing the permanent placement of a lockable clip around a target vessel to interrupt the continuity of the same in a rapid, safe and minimally invasive manner. The apparatus includes a trocar obturator and a hollow member in which the open locking clip is enclosed for delivery to a position proximate to the vas whereupon the trocar obturator is retracted such that the clip is locked onto the vessel to effect occlusion.

6 Claims, 4 Drawing Sheets

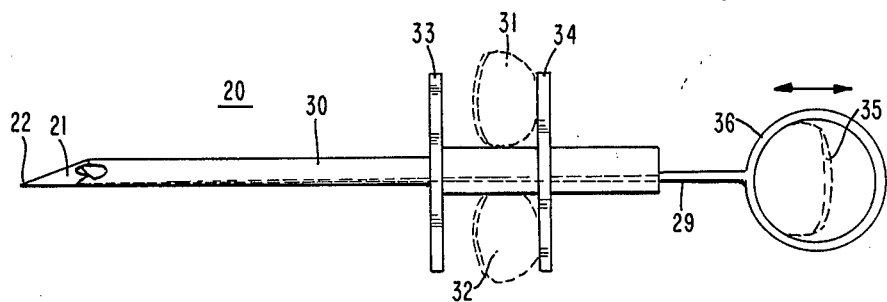
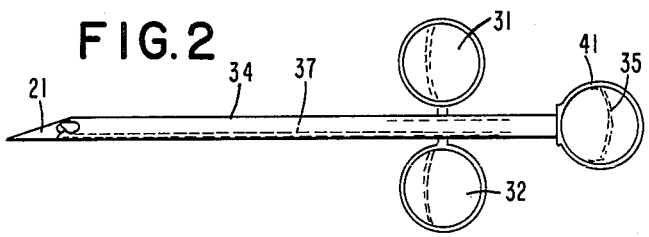
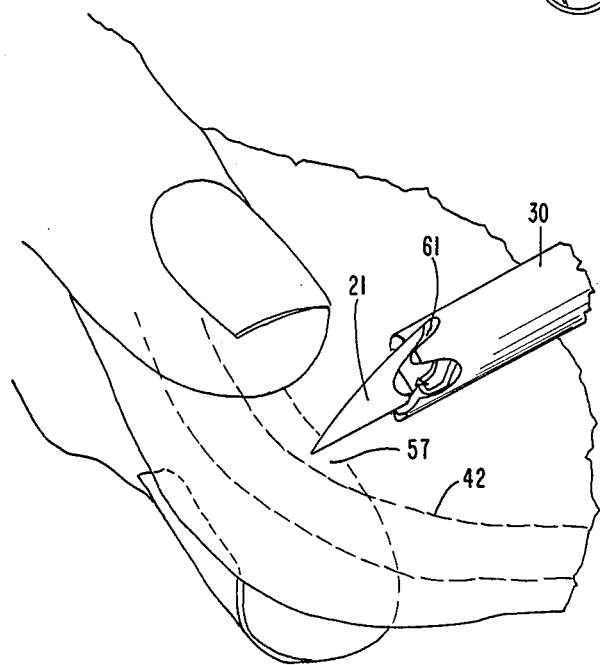

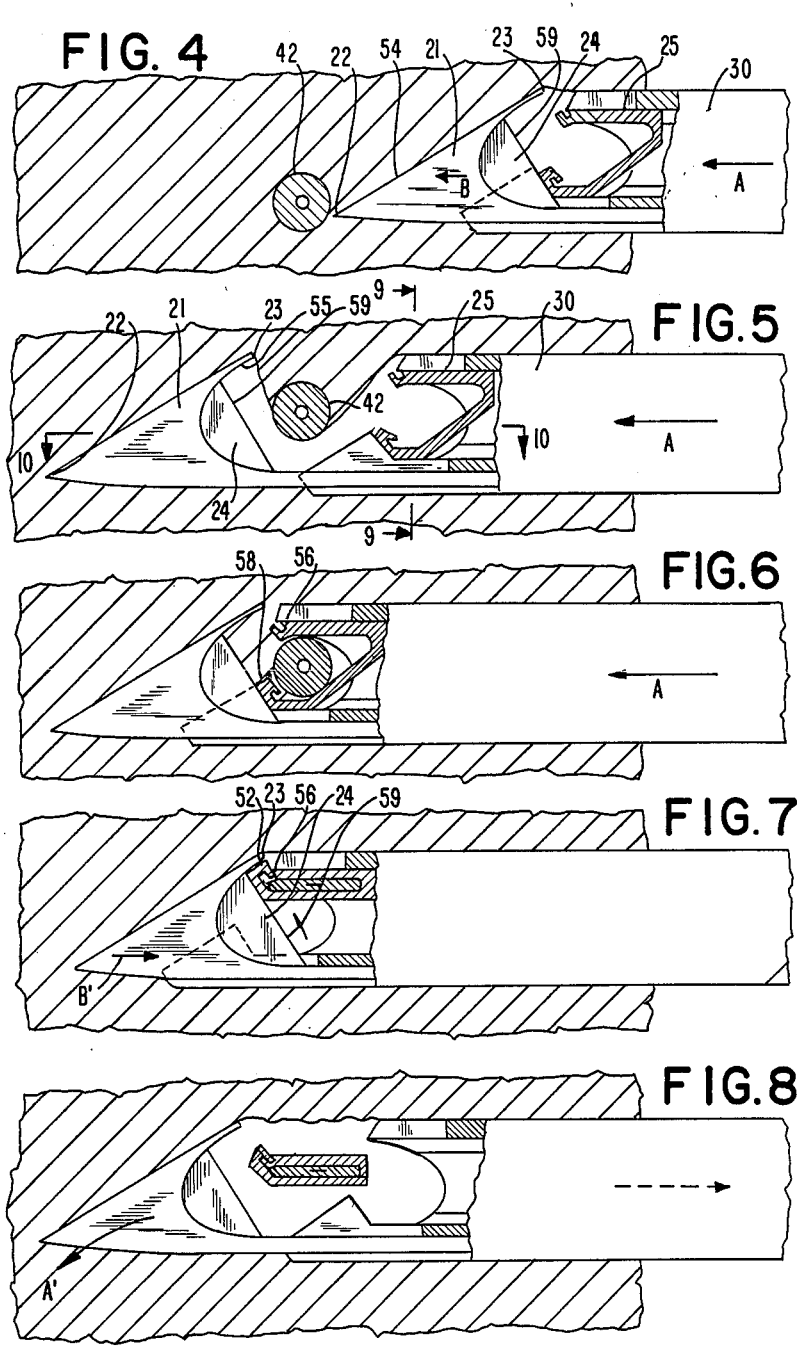

APPARATUS FOR EFFECTING OCCLUSION OF THE VAS DEFERENS

This is a continuation of application Ser. No. 884,417, filed July 11, 1986, now abandoned.

BACKGROUND OF THE INVENTION

The invention relates generally to apparatus for occluding subcutaneous target vessels and, more specifically, to apparatus for occluding the vas deferens in a vasectomy in rapid, safe and minimally invasive manner.

The procedure generally followed in simple vasectomies comprises identifying and then grasping the vas deferens with an appropriate instrument whereupon an incision is made to the adjacent subcutaneous tissue. The vasal sheath is grasped with a clamp and incised with the vas being disected from the sheath. The vas is isolated and a segment is excised whereupon the distal end of the vas is electrocoagulated, suture ligated or clip occluded or a combination thereof, and then buried within the vasal sheath. The proximal end of the vas is electro-coagulated, suture ligated or clip occluded or a combination thereof. Finally, the skin is closed.

Although this procedure has proven to be quite reliable, it is subject to certain disadvantages. More particularly, the above-described procedure is relatively time consuming, requiring on the order of about 40 minutes. The conventional procedure requires a surgical incision which requires all of the precautions normally incident to relatively complicated surgical procedures to be adhered to.

The concept of accomplishing percutaneous occlusion of the vas deferens in a vasectomy by mechanical clip application was disclosed by the present inventor in U.S. Patent No. 4,393,864. This patent describes an apparatus for accomplishing approaching to encompassment, and fixation of the spermatic duct or tubular structure utilizing a trocar instrument with pivotally-actuated jaw members. Although this apparatus is a major improvement in performing vasectomies, it has jaw member movement and clip advancement which may not always be desirable in such a surgical procedure.

OBJECTS AND STATEMENT OF THE INVENTION

Accordingly, one object of the present invention is to provide improved apparatus for use in occluding a vessel in the body, and particularly for occluding the vas deferens in a vasectomy.

Another object of the present invention is to provide improved apparatus whereby a locking clip can be permanently placed around and locked on the vas deferens to interrupt the continuity of the same.

In accordance with this invention means is provided for implanting clips to effect percutaneous occlusion of vessels in vivo, particularly the vas deferens in a vasectomy.

As embodied this means includes a hollow member having a proximal and distal end. The distal end has a means for partially enclosing a target vessel and an open lockable clip aligned in said means. A sliding trocar obturator is positioned for cooperation with the hollow member and is adapted for telescoping movement therein. The sliding trocar obturator has a barb-shaped distal end which extends beyond the distal end of the hollow member. The barb-shaped distal end of the trocar obturator is extended beyond the diameter of the target vessel including a vas deferens. The target vessel is encompassed and captured as the barb-shaped distal end of the trocar obturator is retracted within the hollow member. Upon retraction, the sliding trocar obturator cooperates with the distal end of the hollow member to implant a clip to effect percutaneous occlusion of the target vessel.

DESCRIPTION OF THE DRAWINGS

A more complete appreciation of the present invention and many of the attendant advantages thereof will be readily appreciated as the same becomes better understood by reference to the following detailed description when considered in connection with the accompanying drawings in which:

FIG. 1 is a side elevational view of one embodiment of the present invention.

FIG. 2 is a side elevational view of an alternate embodiment of the present invention.

FIG. 3 is an enlarged perspective view of the forward end of the trocar and sheath of the embodiment shown in FIG. 1 of the present invention.

FIGS. 4 through 8, respectively, are side elevational views in partial cross-section of progressive steps in locating and clipping the vas utilizing the embodiment shown in FIG. 1 of the present invention.

DESCRIPTION OF THE PREFERRED EMBODIMENTS

Figure 9:
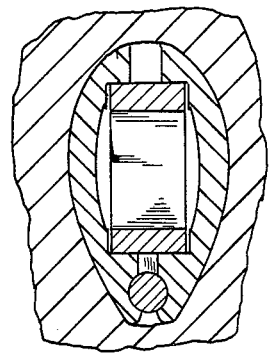
FIG. 9 is a cross-sectional view, taken along the line 9—9 of FIG. 5, showing the clip member contained within the hollow member of one embodiment of the present invention.

Referring now to the figures, one embodiment of the present invention for effecting vas occlusion, generally designated 20, is illustrated in FIG. 1.

Apparatus 20 includes a trocar obturator 21 having a variety of functions including penetrating and cutting through tissue, trapping a target vessel, and holding and implanting a clip on a target vessel.

The penetration function of the trocar obturator 21 is accomplished when the trocar obturator is moved in a forward direction. The trocar obturator is adapted for the penetration of tissue by the provision of barb-shaped end 22 as shown in FIG. 1. The forward movement of the trocar obturator brings the barb-shaped end 22 into contact with the tissue. The pressure resulting from the forward movement of the trocar obturator effects penetration by pushing the barb-shaped end 22 into the tissue.

The cutting of tissue by this embodiment of the trocar obturator occurs in two ways. The first way that tissue can be cut using the trocar obturator is to use the same forward movement of the trocar obturator that resulted in penetration of the tissue. As the trocar obturator 21 is moved forward surface or barb-shaped end 22 cuts through the tissue as shown in FIG. 4. The second way that the trocar obturator cuts through tissue is when the trocar obturator moves in a rearward direction. In this direction, the cutting of the tissue is accomplished by surface or barb-shaped end 23 of the trocar obturator as shown in FIG. 7. The use of these two cutting surfaces enable the trocar obturator to cut tissue in a more efficient manner than art heretofore utilized.

The trapping of a target vessel is accopmlished utilizing the unique design features of the trocar obturator 21. The trocar obturator 21 traps a target vessel by moving forward and going beneath the target vessel. The trocar obturator 21 is moved into position beneath the target vessel and by means of ramp member 54 the target vessel is drawn within the open area behind the trailing edge 55 of the trocar obturator 21.

Holding and implanting of a clip on a target vessel by the trocar obturator utilizes the rearward motion of the trocar obturator 21 and the camming surface 24 which is on the backside of the trocar obturator 21 just below the barb-shaped end 23. As the trocar obturator 21 is moved rearwardly, the camming surface 24 engages the clip 25 to effectively hold the clip in a position that encompasses the target vessel. The trocar obturator 21 is moved further rearwardly so that the clip rides up the incline of the camming surface 24, thereby engaging the clip's barb into a receiving notch and implanting the clip on the target vessel. An alternate location for holding a clip 26 for implantation is in the rearward portion of a trocar obturator 28.

The clip 26 held in trocar obturator 28 is in a position that encompasses the target vessel. The trocar obturator 28 is moved rearwardly so that the clip 26 held in cavity 27 is compressed as the area of cavity 27 is reduced. The rearward motion of the trocar obturator 28 ends with the engaging of the clip's barb into a receiving notch 56 and the implanting of the clip on the target vessel.

In the embodiment shown in FIG. 1, the trocar obturator 21 is positioned on the distal end of slide member 29. Slide member 29 is adapted for telescoping movement within a hollow member 30 to permit controlled longitudinal manipulation of the trocar obturator as needed by the physician. This manipulation of movements is performed by fingers 31 and 32 resting between flanges 33 and 34 formed perpendicular to hollow member 30 and thumb 35 inserted into ring 36 attached to proximal end of slide member 29.

Alternatively, in the embodiment shown in FIG. 2, the trocar obturator 21 is positioned on the distal end of slide member 37. Slide member 37 is adapted for telescoping movement within a hollow member 38 to permit controlled longitudinal manipulation of the trocar obturator as needed by the physician. In the embodiment shown in FIG. 2, this manipulation of movements is performed by fingers 31 and 32 inserted into rings 39 and 40 fixed in a T-configuration to opposite sides of the proximal end of sliding member 37 and thumb 35 inserted into ring 41 attached to the proximal end of hollow member 38.

The surgical procedure wherein the apparatus of the present invention is utilized for effecting vas occlusion, i.e., a vasectomy, utilizing the present invention is accomplished as follows. FIG. 3 shows the approach of the apparatus for effecting vas occlusion. After sterilizing the region of the intended vasectomy 57, a vas diferens 42 is located and firmly held by the physician whereupon the trocar obturator 21 and accompanying hollow member 30 containing an axial notch 61 is introduced through the tissue until the vas deferens is approximated, taking care not to pierce the same.

FIGS. 4-8 illustrate the procedure for implanting locking clips to effect percutaneous occlusion of the vas deferens utilizing the embodiment of the present invention as shown in FIG. 1. Both the hollow member 30 and the trocar obturator 21 are introduced by piercing the skin simultaneously moving both the index and forefinger as well as the thumb in a forward direction as indicated by the arrows A and B located on the hollow member 30 and trocar obturator 21, respectively. The clip 25 is aligned in the hollow member 30 so that one end of the clip 25 rests against the ramp 59 of the camming surface 24 which is in the rearward portion of the trocar obturator 21 as shown in FIG. 4. The hollow member 30 and the trocar obturator 21 continue to move in a forward direction while, simultaneously the trocar obturator 21 is moved in a forward direction so that its barb-shaped end 22 slides underneath the vas deferens 42 as shown in FIG. 5. The vas deferens 42 is now located within the open area between the trailing edge of the trocar obturator 21 and the forward end of the hollow member 30 as shown in FIG. 5. In this position the vas deferens 42 is located between the ramp 59 of the camming surface 24 located in the trocar obturator 21 and the hemispherical cavity of hollow member 30 which contains the clip 25 inserted in its forward region. The trocar obturator 21 is kept stationery and the hollow member 30 is moved forward in that same direction, indicated by the arrow A, such that the vas deferens 42 is now positioned within the confines of the clip 25 as shown in FIG. 6. The movement of the hollow member 30 has trapped the vas deferens within the confines of the clip as the gap is closed between the trocar obturator 21 and the hollow member 30.

Figure 11:
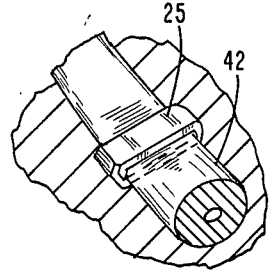
FIG. 11 is a partial perspective view of the implanted clip surrounding the vas.
Figure 10:
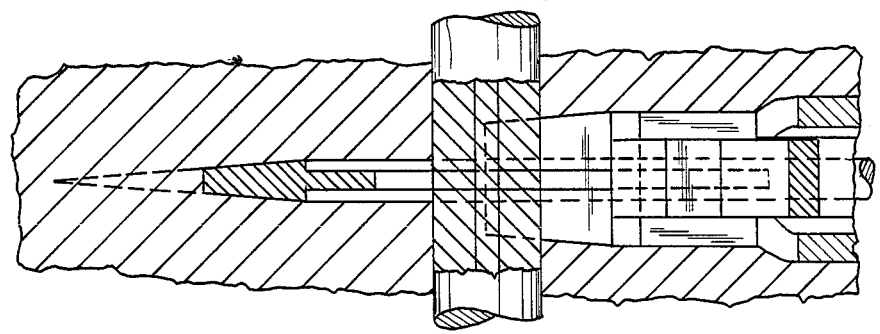
FIG. 10 is a horizontal cross-sectional view taken along the line 10—10 of FIG. 5, showing the relative position of vas with respect to the trocar clip and tubular member.

Upon closure of the gap, slip 25 is aligned in the hollow member 30 so that one end of the clip 25 rests against the ramp 59 of the camming surface 24. Once this has been accomplished, hollow member 30 is held stationary and trocar obturator 21 is retracted as shown by arrow B' in FIG. 7, to cause the ramp 59 of the camming surface 24 to engage the forward edge of the lower jaw member of the cip 25 and effectivley cause it to ride up the ramp 59 of the camming surface 24, thereby engaging the clip's barb 58 into a receiving notch 56 and clamping the vas deferns there between as shown in FIG. 7. The occlusion of the vas deferens is not complete preventing the passage of sperm from the testis to the ejaculatory duct. In FIG. 11 is representation of an implanted clip 25 on the vas deferens 42. Removal is accomplished as shown in FIG. 8 wherein the trocar obturator 21 is moved forward and slightly downwardly, as indicated by the arrow A', permitting the clip 25 to be released from within the confines of the trailing edge of the trocar obturator 21 and the forward edge of the hollow member 30. At this point, the trocar obturator 21 and the hollow member 30 can be withdrawn from within the skin leaving the clipped vas deferens in position. A new clip 25 can then be reinserted into the forward edge of the hollow member 30 and the process repeated. Alternatively, hollow member 30 may be provided with a magazine assembly (not shown) which is capable of holding and presenting a succession of clips to be implanted. This would permit continuous use of the apparatus without requiring removal to effect reloading of a new clip after each implant.

The present invention accomplishes the occlusion of the vas deferens in a rapid manner. Typically under one minute, with minimum invasion of the body.

Figure 12:
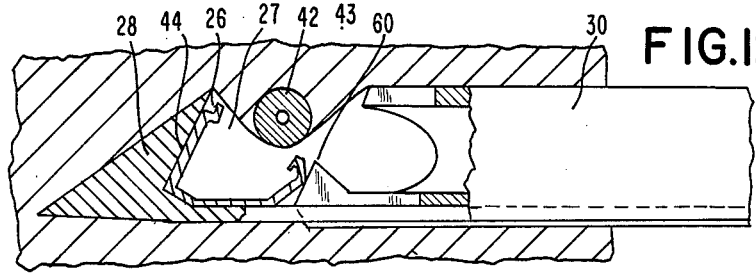
FIG. 12 is a side elevational view in partial cross-section of an alternate embodiment of the present invention.
Figure 13:
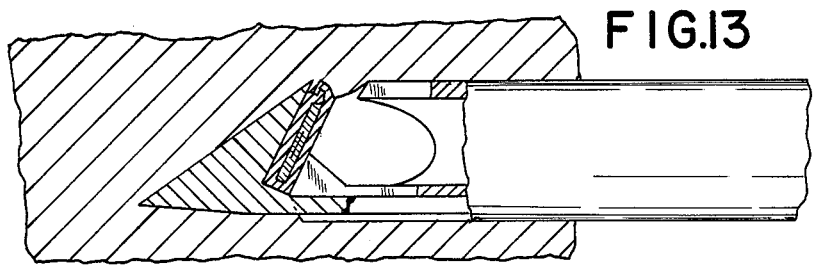
FIG. 13 is a side elevational view in partial cross-section of the embodiment shown in FIG. 12 depicting closure of the clip member around the vas.

An alternate embodiment of the present invention is shown in FIGS. 12 and 13 wherein the clip 26 is located within the trocar obturator 28. This alternate embodiment differs from the embodiment shown in FIG. 1 wherein clip 25 is aligned in the hollow member 30 as shown in FIGS. 4–6. As the trocar obturator 28 moves in a rearward direction, the ramp 60 of the camming surface 43 on the forward end of the hollow member 30 will additionally engage the trailing edge of the clip 26 to lock it into engagement with the vas deferens 42 is located in its proper position. The rearward edge 44 of the the trocar obturator acts as an abutment stop for that leg of the clip 26.

Figure 14:
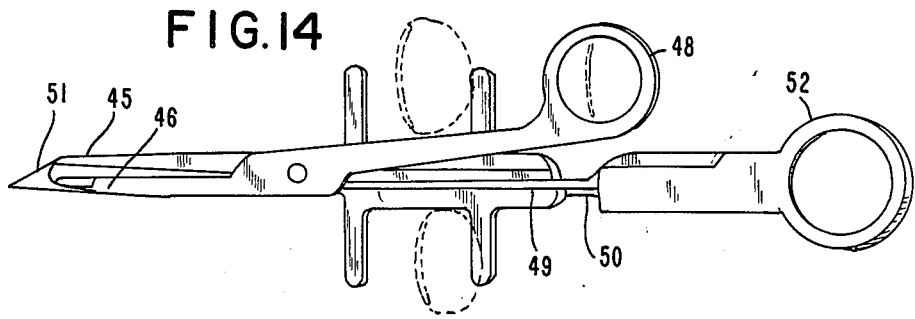
FIG. 14 is a side elevational view of another embodiment of the present invention.
Figure 15:
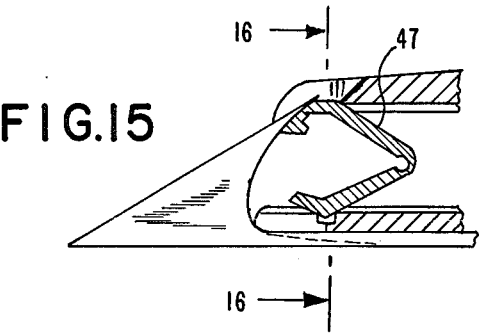
FIG. 15 is an enlarged side elevational view in cross section of the tip end of the embodiment shown in Figure 14.
Figure 16:
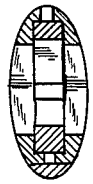
FIG. 16 is a cross-section view of the embodiment shown in FIG. 14 taken along the line 16—16 of FIG. 15.
Figure 17:
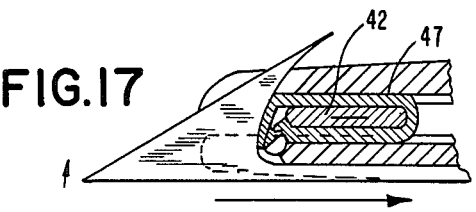
FIG. 17 is a side elevational view in cross section of the embodiment shown in FIG. 14 showing the final stage of clip implantation.

In another advantageous embodiment of the present invention shown in FIGS. 14–17, a pair of jaw members 45 and 46 are interconnected for relative pivotal movement toward and away from each other. The jaw members 45 and 46 are adapted to hold an open clip 47 in operable position to enclose a target vessel 42. The clip 47 has a triangular configuration which is slightly different from the clips above. The clip 47 is located between an upper fixed jaw member 45 and a lower jaw member 46. The lower jaw member 46 retains the bottom portion of the clip 47 while the upper portion of the clip is held in operable position by jaw 45. The clip is inserted as part of a pivoting scissor-like motion which is effected as ring 48 is moved downwardly. This action closes and locks the clip 47 about the vas deferens 42. FIG. 14 illustrates passage 49. This passage 49 enables slide member 50 to have telescoping movement within the lower jaw member 46.

The slide member 50 has, at its distal end, a trocar obturator 51 having a variety of functions including penetrating and cutting through tissue and trapping a target vessel substantially similar in operation to those described above with regard to FIG. 1.

The procedure for implanting locking clips to effect percutaneous occlusion of the vas deferens involves the insert of the trocar obturator 51 in a forward direction by use of ring 52. Ring 52 is attached to the proximal end of the slide member 50 which has at its distal end thr trocar obturator 51. Using the same movements of the trocar obturator 51 as described in the above alternate embodiments, the vas deferens 42 is entrapped within the open clip 47. Open the vas deferens 42 is entrapped within the open clip 47, the lower jaw member 46 will move upwardly as the ring 48 is moved downwardly, thereby effecting a closing of the clip 47 about the vas deferens 42. Movement of the lower jaw member 46 downwardly leaves clip 47 implanted on the vas deferens in the same manner as discussed above in connection with the previous embodiments of the invention.

Although the foregoing description is specifically directed to the use of the present invention in connection with occluding the vas deferens in a vasectomy, it is understood that the apparatus of the invention may be used in connection with other applications.

Obviously, numerous modifications and variations of the present invention are possible in the light of the above teachings. It is therefore to be understood that within the scope of the claims appended hereto, the invention may be practiced otherwise and is specifically disclosed herein.

What is claimed is:

1. Apparatus for implanting locking clips to effect percutaneous occlusion of a target vessel comprising
   a. tissue penetration means including a forward face and a rearward face, said forward face including a barbshaped end portion for penetrating tissue upon forward movement of said tissue penetration means, and said rearward face defining at least a portion of a target vessel chamber, and including a rearwardly facing barb-shaped portion capable of penetrating tissue upon rearward movement of said tissue penetration means
   b. clip retaining means for retaining said locking clip in a predetermined location distal to said rearward face of said tissue penetration means,
   c. camming means disposed within said target vessel chamber for closing said locking clip, and
   d. slide means for obtaining relative slidable movement between said tissue penetration means and said clip retaining means, whereby said tissue penetration means can be used for penetrating tissue substantially entirely around said target vessel, and said tissue penetration means and said clip retaining means can be slidably moved between a first relative position in which said target vessel chamber and said clip retaining means are longitudinally separated from each other, a second relative position in which said target vessel chamber and said clip retaining means are substantially superimposed with each other such that said target vessel located within said target vessel chamber is substantially surrounded, at least in part within said locking clip, and a third relative position in which said locking clip is caused to close upon said target vessel by movement against said camming means so as to effect said occlusion thereof.

2. The apparatus of claim 1 wherein said clip retaining means has a hollow cylindrical configuration, and wherein said tissue penetration means is slidable within said hollow cylindrical configuration of said clip retaining means.

3. The apparatus of claim 1 wherein said direction of said slidable movement comprises a longitudinal direction and wherein said camming means comprises a surface which is angularly disposed with respect to said longitudinal direction.

4. The apparatus of claim 1 wherein said clip retaining means comprises first and second pivotable jaw members.

5. A method for implanting locking clips to effect percutaneous occlusion of a target vessel embedded within surrounding tissue comprising providing an elongated instrument including a barbed-shaped trocar at its distal end and clip retaining means located rearwardly of said barbed-shaped trocar, said method comprising a. providing a locking clip within said clip retaining means, b. isolating said target vessel by cutting trough said surrounding tissue with said barbed shaped trocar, c. slidably separating said barbed-shaped trocar and said clip retaining means so as to create a target vessel chamber therebetween, d. retaining said target vessel within said target vessel chamber, e. slidably bringing together said barbed-shaped trocar and said clip retaining means so as to enclose said target vessel with said locking clip, and f. further slidably bringing together said barbed shaped trocar and said clip retaining means so as to close said locking clip upon said target vessel in order to effect said occlusion thereof.

6. The method of claim 5 including subsequently slidably separating said barbed-shaped trocar from said clip retaining means so as to free said occluded target vessel.

* * * * *

UNITED STATES PATENT AND TRADEMARK OFFICE
CERTIFICATE OF CORRECTION

PATENT NO.   :   4,877,028
DATED        :   October 31, 1989
INVENTOR(S)  :   Jeffrey Sandhaus It is certified that error appears in the above-identified patent and that said Letters Patent is hereby corrected as shown below:

Column 1, line 37, delete "4,393,864" and insert therefor --4,394,864--.

Column 1, line 38, "approaching" should read --approach--.

Column 4, line 49, delete "slip" and insert therefor --clip--.

Column 4, line 59, "deferns" should read --deferens--.

Column 5, line 61, delete "Open" and insert therefor --Once--.

Column 7, line 4, delete "trough" and insert therefor --through--.

Signed and Sealed this

Ninth Day of October, 1990

Attest:

*Attesting Officer*

HARRY F. MANBECK, JR.

*Commissioner of Patents and Trademarks*